US012672980B2

(12) United States Patent
Qiu

(10) Patent No.: US 12,672,980 B2
(45) Date of Patent: Jul. 7, 2026

(54) ANTI-SNORING PILLOW

(71) Applicant: Shenzhen Weirui Technology Co., Ltd., Shenzhen (CN)

(72) Inventor: Jiliang Qiu, Shaoguan (CN)

(73) Assignee: Shenzhen Weirui Technology Co., Ltd., Shenzhen (CN)

( * ) Notice: Subject to any disclaimer, the term of this patent is extended or adjusted under 35 U.S.C. 154(b) by 24 days.

(21) Appl. No.: 18/924,417

(22) Filed: Oct. 23, 2024

(65) Prior Publication Data

US 2025/0213386 A1 Jul. 3, 2025

(30) Foreign Application Priority Data

Dec. 29, 2023 (CN) .......................... 202311840694.5

(51) Int. Cl.
*A61F 5/56* (2006.01)
*A47G 9/10* (2006.01)
(52) U.S. Cl.
CPC .............. *A61F 5/56* (2013.01); *A47G 9/1027* (2013.01)
(58) Field of Classification Search
CPC .. A47G 9/1027; A47G 9/10; A47G 2200/226; A47G 2009/003; A61F 5/56
See application file for complete search history.

(56) References Cited

U.S. PATENT DOCUMENTS

| | | | | | |
|---|---|---|---|---|---|
| 10,448,765 | B2 * | 10/2019 | Zhang | ...................... | H04W 4/80 |
| 10,820,728 | B1 * | 11/2020 | Rao | ........................... | A47G 9/10 |
| 11,160,683 | B2 * | 11/2021 | Nunn | ..................... | A47C 31/00 |
| 2009/0089932 | A1 * | 4/2009 | Chen | ......................... | A61F 5/56 |
| | | | | | 5/640 |
| 2020/0405525 | A1 * | 12/2020 | Yu | ............................. | A61F 5/56 |
| 2024/0374058 | A1 * | 11/2024 | Han | ..................... | A47G 9/1027 |
| 2025/0213386 | A1 * | 7/2025 | Qiu | ........................... | A61F 5/56 |

FOREIGN PATENT DOCUMENTS

EP 3123931 A1 * 2/2017 .............. A61F 5/56

* cited by examiner

*Primary Examiner* — J. T. Newton
(74) *Attorney, Agent, or Firm* — JEEN IP LAW, LLC

(57) ABSTRACT

Disclosed is an anti-snoring pillow, including a pillow bottom plate, a sleeping posture sensor is fixedly connected to a lower surface of the pillow bottom plate, and a sleeping posture airbag and a main control box are fixedly connected to an upper surface of the pillow bottom plate, wherein a head position sensor is fixedly connected to an upper surface of the sleeping posture airbag, an anti-snoring airbag is fixedly connected to an upper surface of the head position sensor, and the main control box is in communication connection with an air pump box, the air pump box is connected to the sleeping posture airbag and the anti-snoring airbag through pipelines, and wherein the sleeping posture sensor and the head position sensor are in communication connection with the main control box, and a pillow support-ing cotton is provided on the upper surface of the pillow bottom plate.

6 Claims, 7 Drawing Sheets

5

8

9

ANTI-SNORING PILLOW

CROSS-REFERENCE TO RELATED APPLICATIONS

This application claims priority to Chinese Patent Application No. 202311840694.5, filed on Dec. 29, 2023, which is hereby incorporated by reference in its entirety.

TECHNICAL FIELD

The present disclosure relates to a product for sleeping, in particular, to an anti-snoring pillow.

BACKGROUND

Snoring is a common sleep phenomenon that often interferes with the sleep of others. If a person is far away from a snorer and cannot touch the snorer, it is difficult to stop the snorer by just shouting. On the one hand, shouting of the high sound level may be useless for a sleeping person because of a lack if energy; on the other hand, shouting of the high sound level is undesired when considering other people's sleep. Therefore, the phenomenon of snoring has always been a difficult problem for people.

Pillows currently on the market can only solve the problem of snoring, but they provide poor sleep comfort, can not adapt to the sleeping position, and may be harm to shoulders and cervical spine after long-term use.

SUMMARY

The purpose of the present disclosure is to solve at least one of the technical problems existing in the prior art. The present disclosure provides an anti-snoring pillow, which can adapt to sleeping postures, such as sleeping on the back and on the side, which also solves a problem of sleeping snoring, relieves snoring, protects cervical vertebrae and shoulders, and enhances the comfort of sleep.

The present disclosure provides an anti-snoring pillow, including a pillow bottom plate, a sleeping posture sensor is fixedly connected to a lower surface of the pillow bottom plate, and a sleeping posture airbag and a main control box are fixedly connected to an upper surface of the pillow bottom plate, wherein a head position sensor is fixedly connected to an upper surface of the sleeping posture airbag, an anti-snoring airbag is fixedly connected to an upper surface of the head position sensor, and the main control box is in communication connection with an air pump box, the air pump box is connected to the sleeping posture airbag and the anti-snoring airbag through pipelines, and wherein the sleeping posture sensor and the head position sensor are in communication connection with the main control box, and a pillow supporting cotton is provided on the upper surface of the pillow bottom plate. Through the above components, the sleeping posture is sensed by the sleeping position sensor, and then the height is adjusted by the sleeping posture airbag to adapt to the sleeping posture. The snore is then detected and the head position is adjusted by the anti-snoring airbag to relieve snoring.

In some embodiments, the anti-snoring airbag is provided as a plurality of anti-snoring airbags, and air valves are arranged at connection points of the plurality of anti-snoring airbags and the air pump box, wherein the anti-snoring airbag and the sleeping posture airbag are provided with an air pressure sensor inside. Through the above components, air pressure of the anti-snoring airbag at different locations are adjustable.

In some embodiments, the sleeping posture sensor, the sleeping posture airbag, the main control box, the head position sensor, and the anti-snoring airbag are all located inside the pillow supporting cotton, and the pillow supporting cotton has curved surfaces. Through the above components, the user may be more comfort.

In some embodiments, a microphone is provided inside the main control box, and the air valve is located inside the main control box. Through the above components, the user's snore may be detected to facilitate subsequent adjustment.

In some embodiments, the sleeping posture sensor is arranged at a front end of the pillow base plate, and the sleeping posture sensor is configured to be in contact with a shoulder. Through the above components, the user's sleeping posture is detectable, such as, sleep on one's side, lying.

In some embodiments, each of the sleeping posture sensor and the head position sensor is provided with a pressure sensor at a surface thereof. Through the above components, stress distribution during sleep can be detected.

The anti-snoring pillow can be used as following steps:

S1. charging the pillow, placing the pillow on a bed, and a user pillows on the pillow;

S2. realizing anti-snoring: when detecting that the user is snoring, through the microphone, the main control box senses head pressure distribution information through the head position sensor, so as to determine a head position, and then the corresponding anti-snoring airbag is cyclically inflated and deflated to change a height of the surface of the pillow, causing the user's head to rotate to a certain angle, unblocking a respiratory channel of a throat, promoting smooth breathing, and relieving snoring;

S3. realizing sleeping posture adaptation: the main control box senses and obtains shoulder pressure distribution information through the sleeping posture sensor, determines user's sleeping posture, and an air pressure sensor detects a pressure of the sleeping posture airbag, and compares the pressure with a preset air pressure under each sleeping posture; if the detected air pressure is less than the preset air pressure, the airbag is inflated, and if the detected air pressure is greater than the preset air pressure, the airbag is deflated, so as to realize adjustment of the pillow height to adapt to the sleeping posture.

Beneficial Effects 1, the present disclosure, through the snoring detection technology, the sleeping posture recognition technology, the airbag inflation and deflation control technology, the air pressure monitoring technology, through the integration and optimization application of the series of technologies, achieves the purpose of alleviating sleep snoring and adapting the sleeping posture.

2, the present disclosure can adapt to sleeping postures such as sleeping on the back and side while solving the problem of sleeping snoring, so as to alleviate the phenomenon of snoring and at the same time protect the cervical vertebrae and shoulders, and adapt to improve the comfort of sleep.

BRIEF DESCRIPTION OF DRAWINGS

The present disclosure is further described below in connection with the accompanying drawings and embodiments.

REFERENCE LIST

1—main control box; 2—sleeping posture sensor; 3—head position sensor; 4—air valve; 5—air pump box; 6—sleeping posture airbag; 7—anti-snoring airbag; 8—pillow supporting cotton; 9—pillow bottom plate; 10—microphone; 11—air pressure sensor.

DESCRIPTION OF EMBODIMENTS

This part will describe in detail the specific embodiments of the present disclosure, some embodiments of the present disclosure are shown in the accompanying drawings, the accompanying drawings are used to supplement the description of the textual portion of the specification with graphics, so that a person can intuitively and imaginatively understand each of the technical features of the present disclosure and the overall technical scheme, but these features or solutions cannot be construed as a limitation on the scope of protection of the present disclosure.

Figure 1:
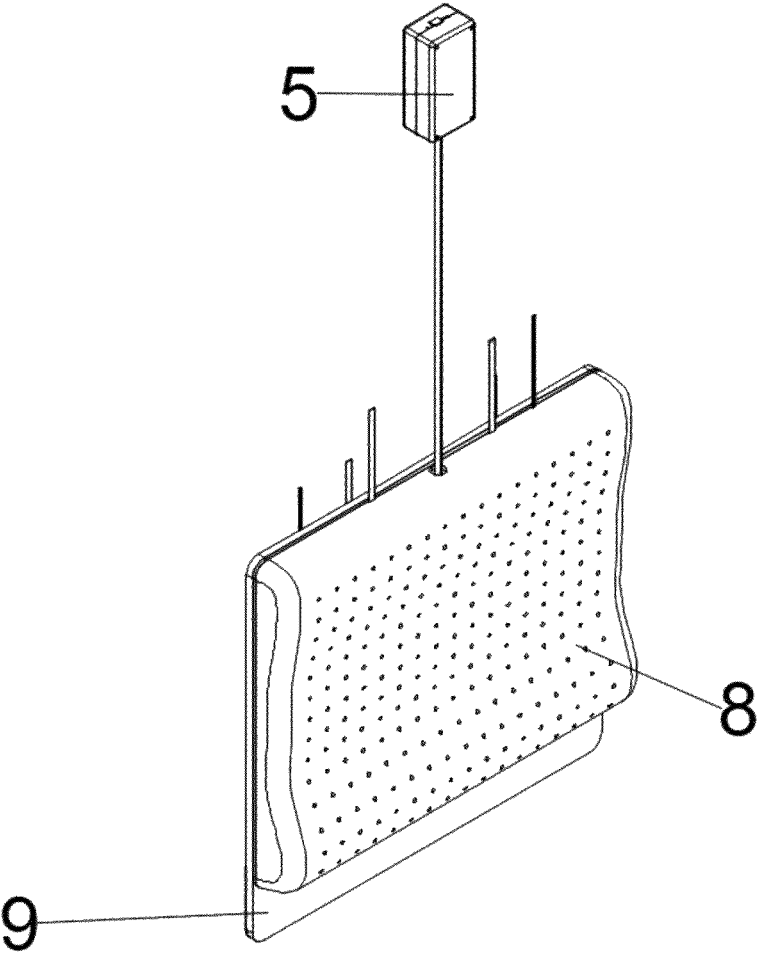
FIG. 1 shows an overall structural diagram of the anti-snoring pillow according to embodiments of the present disclosure.
Figure 2:
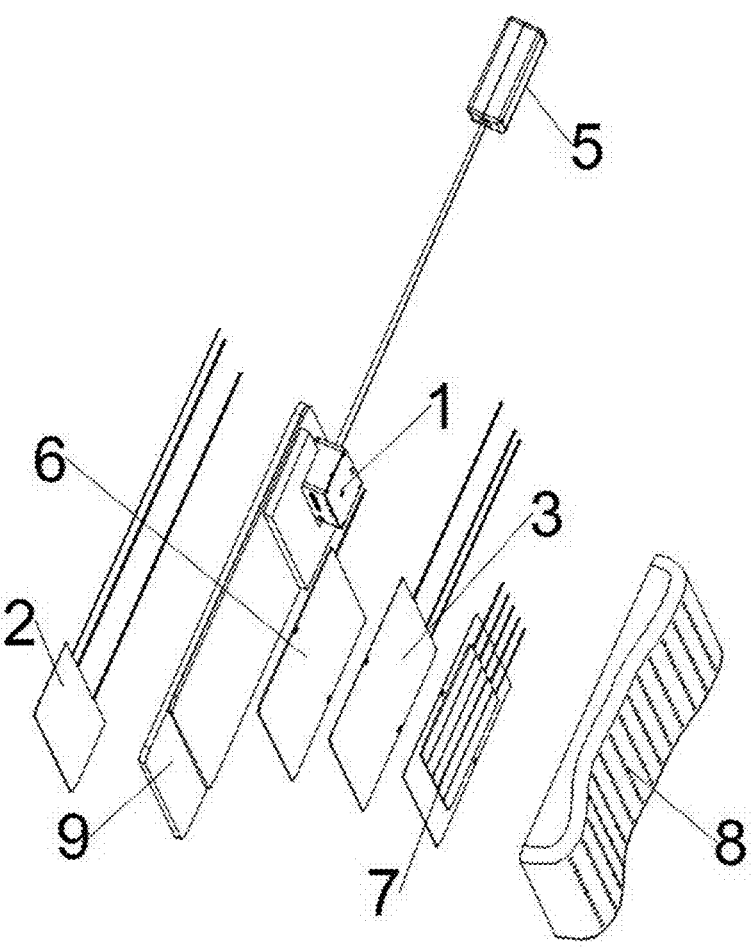
FIG. 2 shows an exploded view of the anti-snoring pillow according to embodiments of the present disclosure.
Figure 3:
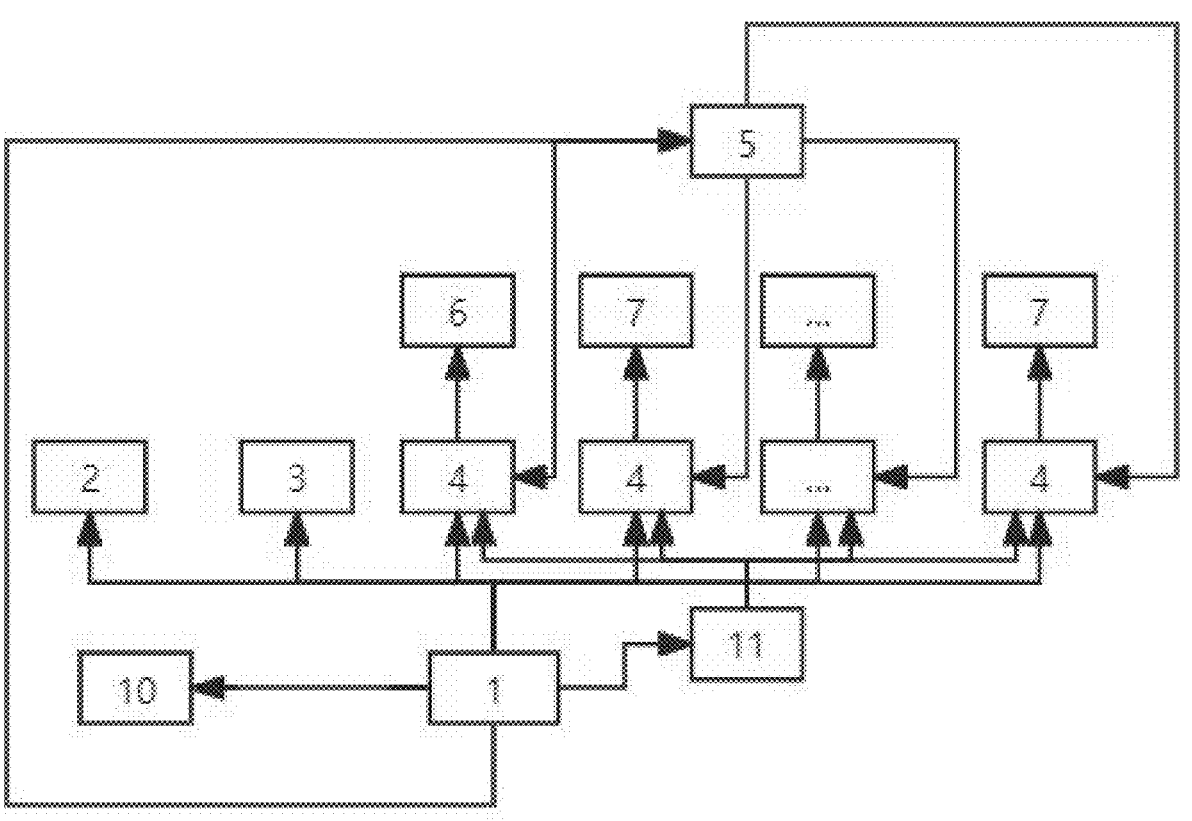
FIG. 3 is a controlling diagram of a sleeping position airbag and an anti-snoring airbag of the anti-snoring pillow according to embodiments of the present disclosure.
Figure 4:
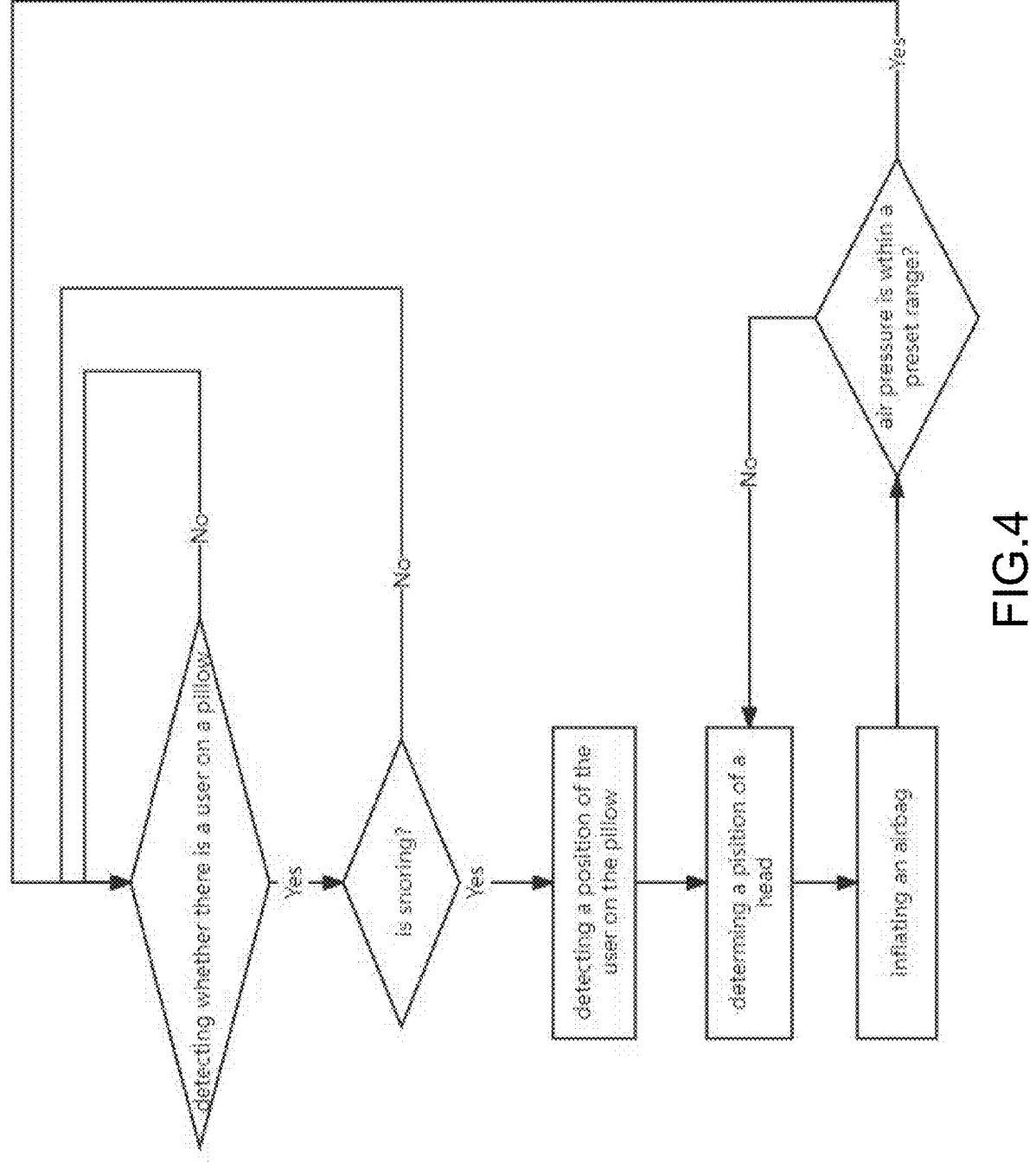
FIG. 4 shows a snoring adjustment judgment diagram of the anti-snoring pillow according to embodiments of the present disclosure.
Figure 5:
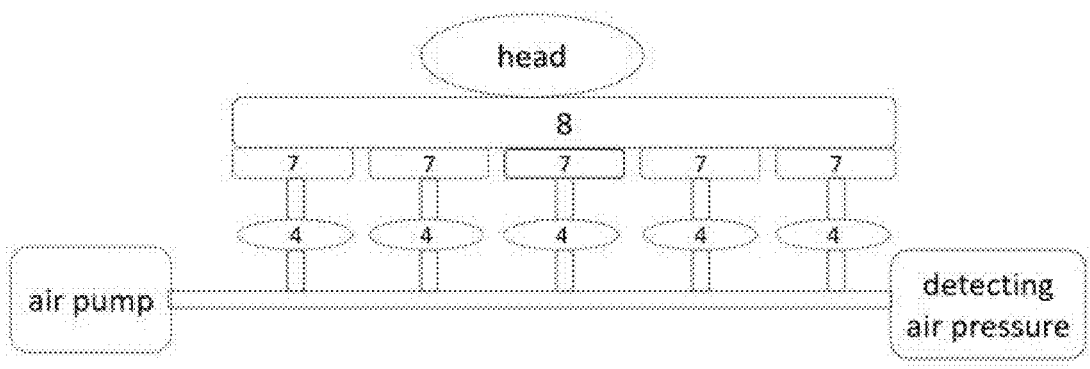
FIG. 5 shows a diagram of the anti-snoring action of the anti-snoring pillow according to embodiments of the present disclosure.
Figure 5:
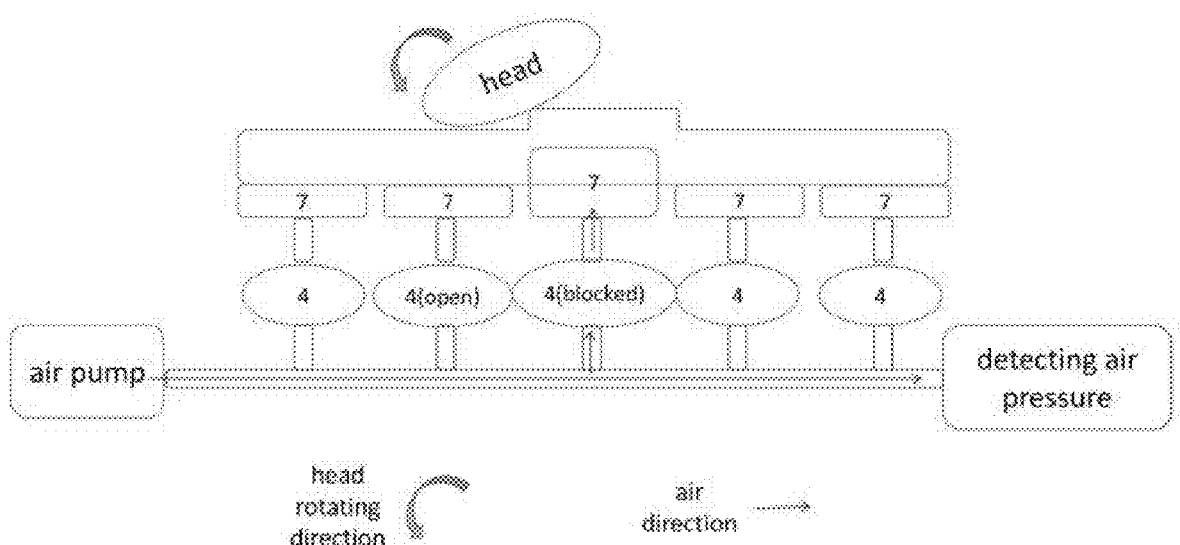
Figure 6:
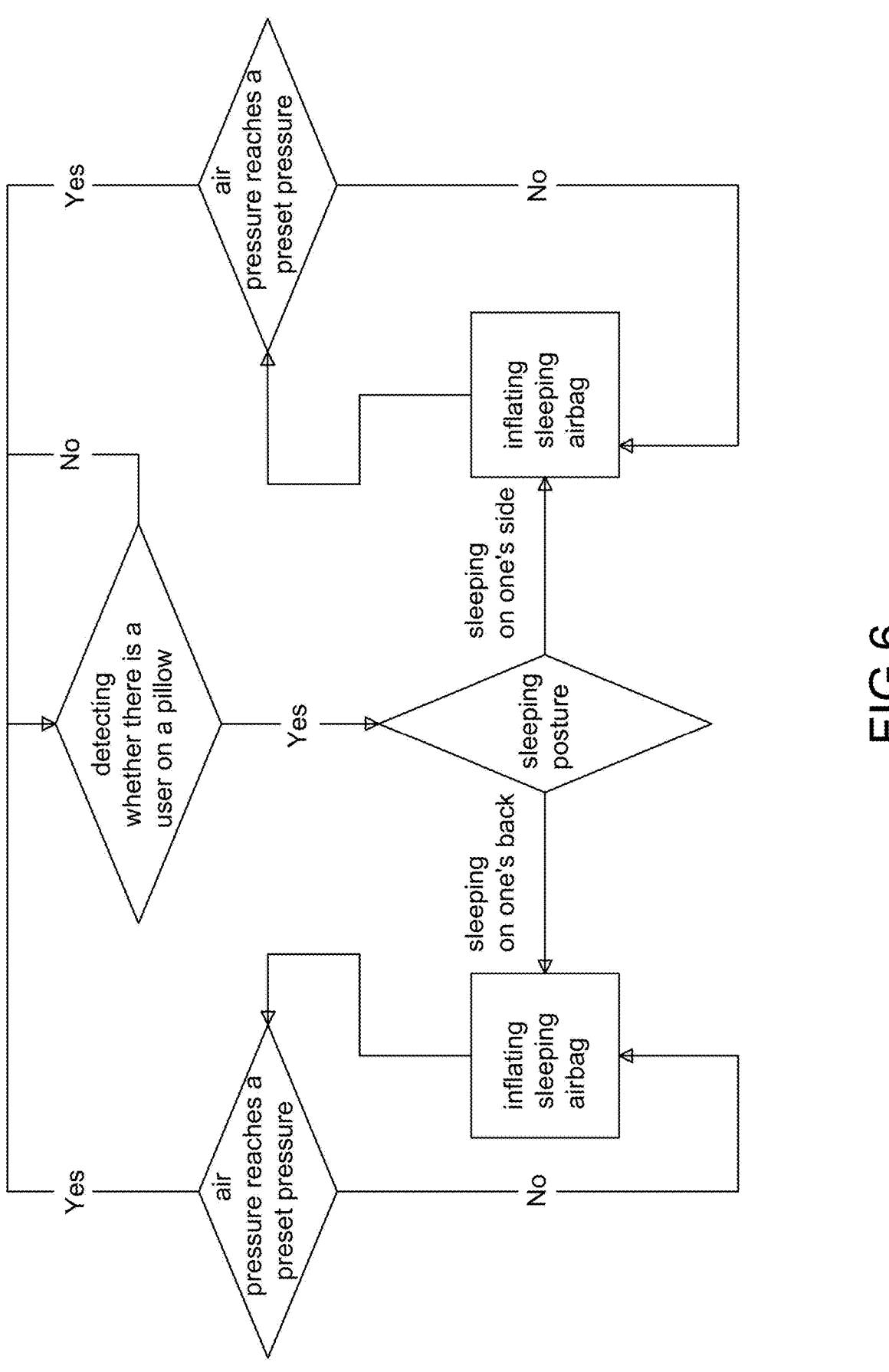
FIG. 6 shows a diagram of the sleeping position adjustment judgment of the anti-snoring pillow according to embodiments of the present disclosure.
Figure 7:
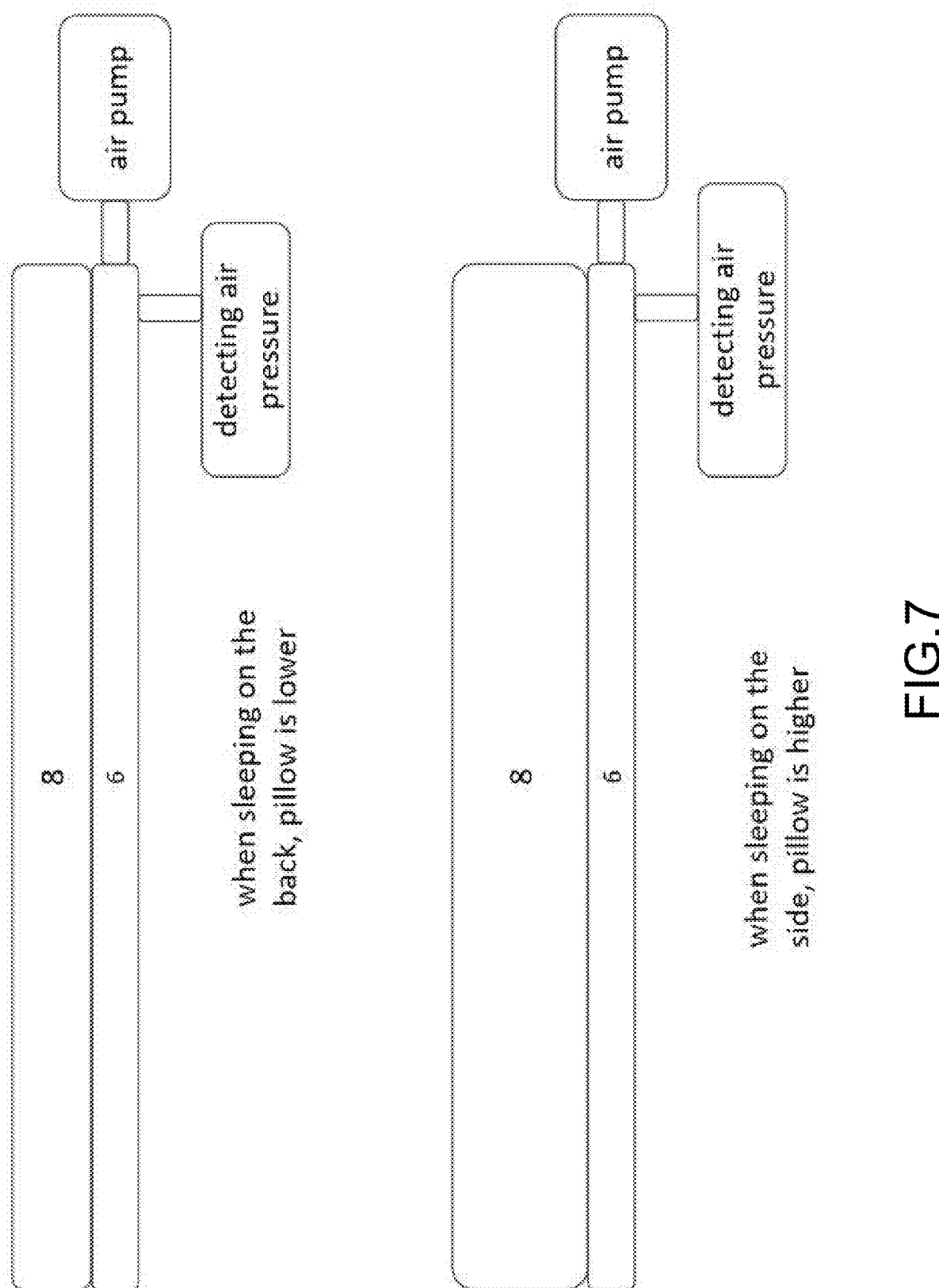
FIG. 7 shows a diagram of the sleeping posture action of the anti-snoring airbag according to embodiments of the present disclosure.

Referring to FIGS. 1-7, an embodiment of the present disclosure provides an anti-snoring pillow including a pillow base plate 9, the pillow base plate 9 is used for placing and fixing some components, a sleeping posture sensor 2 is fixedly connected to a lower surface of the pillow base plate 9, the sleeping posture sensor 2 is arranged at a front end of the pillow base plate 9, the sleeping posture sensor 2 is in contact with a shoulder (such as, a shoulder of a person who is lying on the pillow), and when a person is lying on the pillow, the sleeping posture sensor 2 can sense force distribution at the shoulder, and the sleeping posture can be determined by the force distribution information. An upper surface of the pillow base plate 9 is fixedly connected with a sleeping posture airbag 6 and the main control box 1, the main control box 1 is provided with a microphone 10 inside the main control box 1, which functions in detect sound in the environment. The main control box 1 can determine whether the user is snoring or not by recognizing the sound information picked up by the microphone 10. An air valve 4 is located inside the main control box 1. A head position sensor 3 is fixedly connected to the upper surface of the sleeping airbag 6, and pressure sensors are distributed on surfaces of the sleeping position sensor 2 and the head position sensor 3 to detect the pressure distribution of the head and the shoulders, and the pressure distribution on the pillow supporting cotton 8 can be detected, and the head position on the pillow can be determined through the pressure distribution. A plurality of anti-snoring airbags 7 are fixedly connected to the upper surface of the head position sensor 3, air valves 4 are arranged at connections between the plurality of anti-snoring airbags 7 and an air pump box 5. The air valve 4 is arranged in the main control box 1, which is used for controlling the inflation and deflation of the sleeping airbag 6 and the anti-snoring airbag 7, wherein each of the airbags is at least connected with a solenoid valve (through a structure) to realize independent control of inflation and deflation for each of the airbags, and the anti-snoring airbag 7 and the sleeping airbag 6 are provided with a barometric pressure sensor 11 placed in the main control box 1, and the function of which is to detect the air pressure value during the inflation and deflation of sleeping airbag 6 and anti-snoring airbag 7. The main control box 1 is connected to the air pump box 5, the air pump is placed in the air pump box 5, connected to the air valve 4 through the structure to inflate the airbag. The air pump box 5 is connected to the sleeping airbag 6 and the anti-snoring airbag 7 through pipeline, the sleeping posture sensor 2 and the head position sensor 3 are each in communication connection to the main control box 1, and the upper surface of the pillow base plate 9 is provided with the pillow supporting cotton 8, and the pillow supporting cotton 8 is used to comfort the head and support the shoulders.

The sleeping position sensor 2, the sleeping position airbag 6, the main control box 1, the head position sensor 3, and the anti-snoring airbag 7 are all located inside the pillow supporting cotton 8, and the surface of the pillow supporting cotton 8 is configured as a curved surface.

an anti-snoring pillow may be used as follows:

S1. charging the pillow, placing the pillow on a bed, and a user pillows on the pillow;

S2. realization of stopping snoring: when it is detected that the user is snoring through the microphone 10, the main control box 1 senses and obtains the head pressure distribution information through the head position sensor 3, so as to determine the head position, and then the corresponding anti-snoring airbag 7 is cyclically inflated and deflated to change the height of the surface of the pillow, which causes the user's head to rotate to a certain angle, unblocks the respiratory channel of the throat, promotes smooth breathing, and relieves snoring;

S3. sleeping posture adaptation realization: the main control box 1 senses and obtains the shoulder pressure distribution information through the sleeping posture sensor 2, determines the user's sleeping posture, the air pressure sensor 11 detects the pressure value of the sleeping posture airbag 6, and compares the pressure value with the preset air pressure value under each sleeping posture, if the detected air pressure value is less than the preset air pressure value, the airbag is inflated, and if the detected air pressure value is greater than the preset air pressure value, the airbag is deflated, so as to realize the adjustment of the pillow height, in order to adapt to the sleeping posture.

The embodiments of the present disclosure are described in detail above in conjunction with the accompanying drawings, but the present disclosure is not limited to the above embodiments, and various changes can be made without departing from the purpose of the present disclosure within the scope of the knowledge possessed by persons of ordinary skill in the said technical field.

What is claimed is:

1. An anti-snoring pillow, comprising a pillow bottom plate, a sleeping posture sensor is fixedly connected to a lower surface of the pillow bottom plate, and a sleeping posture airbag and a main control box are fixedly connected to an upper surface of the pillow bottom plate, wherein a head position sensor is fixedly connected to an upper surface of the sleeping posture airbag, an anti-snoring airbag is fixedly connected to an upper surface of the head position sensor, and the main control box is in communication connection with an air pump box, the air pump box is connected to the sleeping posture airbag and the anti-snoring airbag through pipelines, and wherein the sleeping posture sensor and the head position sensor are in communication connection with the main control box, and a pillow support- ing cotton is provided on the upper surface of the pillow bottom plate.

2. The anti-snoring pillow according to claim 1, wherein the anti-snoring airbag is provided as a plurality of anti- snoring airbags, and air valves are arranged at connection points of the plurality of anti-snoring airbags and the air pump box, wherein the anti-snoring airbag and the sleeping posture airbag are provided with an air pressure sensor inside.

3. The anti-snoring pillow according to claim 2, wherein a microphone is provided inside the main control box, and the air valve is located inside the main control box.

4. The anti-snoring pillow according to claim 3, wherein each of the sleeping posture sensor and the head position sensor is provided with a pressure sensor at a surface thereof.

5. The anti-snoring pillow according to claim 1, wherein the sleeping posture sensor, the sleeping posture airbag, the main control box, the head position sensor, and the anti- snoring airbag are all located inside the pillow supporting cotton, and the pillow supporting cotton has curved surfaces.

6. The anti-snoring pillow according to claim 1, wherein the sleeping posture sensor is arranged at a front end of the pillow base plate, and the sleeping posture sensor is con- figured to be in contact with a shoulder.

\* \* \* \* \*